United States Patent [19]

Pearson et al.

[11] Patent Number: 6,162,915

[45] Date of Patent: Dec. 19, 2000

[54] PROCESS FOR HETEROCYCLIC SULFONYL CHLORIDE COMPOUNDS

[75] Inventors: Douglas L. Pearson; Jimmy J. Tai; Timothy J. Adaway, all of Midland, Mich.

[73] Assignee: Dow AgroSciences LLC, Indianapolis, Ind.

[21] Appl. No.: 09/104,610

[22] Filed: Jun. 25, 1998

Related U.S. Application Data

[60] Provisional application No. 60/050,873, Jun. 26, 1997.

[51] Int. Cl.$^7$ ............ C07D 487/00; C07D 205/00; C07D 213/00; C07D 293/00; A01A 43/90

[52] U.S. Cl. ............... 544/263; 544/3; 544/14; 544/179; 544/180; 544/224; 544/200; 544/450; 544/484; 546/1; 546/28; 546/184; 548/100; 548/122; 548/250; 548/255; 549/9; 549/13; 549/29; 549/88; 549/90; 549/200; 504/241

[58] Field of Search ................... 544/263, 3, 14, 544/179, 180, 224; 504/241; 540/200, 450, 484; 546/1, 28, 184; 548/100, 122, 250, 255; 549/9, 13, 29, 88, 90, 200

[56] References Cited

U.S. PATENT DOCUMENTS

| | | | |
|---|---|---|---|
| 5,008,396 | 4/1991 | Krauss | 548/263.8 |
| 5,488,109 | 1/1996 | Olmstead et al. | 544/263 |

FOREIGN PATENT DOCUMENTS

| | | |
|---|---|---|
| 0142811 | 5/1985 | European Pat. Off. . |
| 0727424 A2 | 8/1996 | European Pat. Off. . |
| 4-283568 | 10/1992 | Japan . |

OTHER PUBLICATIONS

H. J.–M. Dou et al., C. R. Academy of Sciences Paris, 284, 685–688 (1977).

*Primary Examiner*—Mukund J. Shah
*Assistant Examiner*—Tamthom N. Truong
*Attorney, Agent, or Firm*—Craig E. Mixan

[57] ABSTRACT

Chlorosulfonyl substituted aromatic heterocyclic compounds, such as 2-chlorosulfonyl[1,2,4]triazolo[1,5-c] pyrimidine compounds, were prepared in good yield by chloroxidation of di(aromatic heterocyclyl) disulfide compounds in a medium containing water, a water-immiscible organic solvent, and a phase transfer catalyst, such at tetrabutylammonium chloride.

13 Claims, No Drawings

PROCESS FOR HETEROCYCLIC SULFONYL CHLORIDE COMPOUNDS

CROSS-REFERENCE TO RELATED APPLICATIONS

This application claims the benefit of U.S. Provisional Application No. 60/050,873, filed Jun. 26, 1997.

BACKGROUND OF THE INVENTION

The present invention is directed to a process for preparing heterocyclic sulfonyl chloride compounds by chloroxidation of di(heterocyclyl) disulfide compounds.

The preparation of a number of heterocyclic sulfonyl chloride compounds (chlorosulfonyl substituted heterocycle compounds) from di(heterocyclyl) disulfide compounds (dithiobis(heterocycle) compounds) by reaction with chlorine in an aqueous acidic medium, a process type generally known as chloroxidation, has been disclosed in the art, for example, in U.S. Pat. Nos. 5,008,396 and 5,488,109. The disclosed chloroxidation procedures, however, give poor results when applied to the preparation of many heterocyclic sulfonyl chloride compounds from corresponding di(heterocyclyl) disulfide compounds. Low yields, for example, are typically observed in the preparation of heterocyclic sulfonyl chloride compounds from di(heterocyclyl) disulfide compounds that have little solubility in the reaction medium employed or that have other substituents that are reactive under the process conditions required. The discovery of a high yield process for converting a broad range of di(heterocyclyl) disulfide compounds to heterocyclic sulfonyl chloride compounds would be highly desirable.

SUMMARY OF THE INVENTION

It has now been found that di(heterocyclyl) disulfide compounds, including those that possess sensitive substituents and/or have little solubility in aqueous acids or common organic solvents can be converted to heterocyclic sulfonyl chloride compounds in good yield by chloroxidation of the corresponding di(heterocyclyl) disulfide compound if the reaction is carried out in a medium comprising a water-immiscible organic solvent, water, and a phase transfer catalyst.

The process of the invention includes the preparation of a chlorosulfonyl substituted aromatic heterocycle compound of Formula I:

wherein HET represents an optionally substituted 5- or 6-membered aromatic heterocyclic moiety
which comprises contacting a di(aromatic heterocyclyl)-disulfide compound of Formula II:

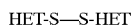

wherein HET is defined as for compounds of Formula I with chlorine in a medium comprising a water-immiscible organic solvent, water, and an effective amount of a phase transfer catalyst at a temperature of about −20° C. to about 60° C.

Tetraalkylammonium salts are often preferred phase transfer catalysts and chlorinated hydrocarbon solvents are often preferred water-immiscible organic solvents. Temperatures of about −10° C. to about 30° C. are typically preferred. The process is advantageously applied to the preparation of many substituted 2-chlorosulfonyl[1,2,4]triazolo[1,5-c]pyrimidine compounds.

DETAILED DESCRIPTION OF THE INVENTION

The process of the present invention is well suited for the preparation of a broad variety of chlorosulfonyl substituted aromatic heterocycle compounds of Formula I. It is especially useful for the preparation of such compounds when the di(aromatic heterocyclyl)-disulfide compound of Formula II starting material is relatively insoluble in common water-immiscible organic solvents that are suitable for use in chloroxidation reaction media and in aqueous hydrochloric acid. Compounds of Formula II that are relatively insoluble include those that are less than about 5 percent soluble in aliphatic chlorinated hydrocarbon solvents or aqueous hydrochloric acid at temperatures below about 30° C. The process is more especially useful when the solubility of the di(aromatic heterocyclyl)disulfide compound of Formula II in the reaction medium is less than about 1 percent at temperatures below about 30° C. The process is also especially useful for the preparation of compounds of Formula I that react with either chloroxidation reagents or media under typical chloroxidation reaction conditions to produce undesirable by-products. Such sensitive compounds include compounds of Formula I having substituents that react readily with hydrogen chloride or chlorine.

Suitable heterocyclic moieties encompassed by the term HET of Formulas I and II are inclusive of 5- and 6-membered aromatic heterocyclic moieties, including 5-and 6-membered aromatic heterocyclic moieties that are fused to benzene (benzoheterocyclic moieties) or fused to 5- and 6-membered aromatic heterocyclic compounds (heterocycloheterocyclic moieties). Oxygen, sulfur, and nitrogen heteroatoms may be present in the heterocyclic moieties, HET. In general, each single ring heterocyclic and benzoheterocyclic 5- or 6-membered aromatic moiety HET may possess one oxygen or one sulfur atom and up to three nitrogen atoms and each heterocycloheterocyclic 5- or 6-membered aromatic moiety HET (HET consists of two fused heterocyclic rings) may possess a total of up to two atoms selected from oxygen and sulfur and up to six nitrogen atoms. For example, the process can be applied to prepare a wide variety of chlorosulfonyl substituted oxazoles, isoxazoles, thiazoles, isothiazoles, pyrazoles, imidazoles, 1,3,4-oxadiazoles, 1,3,4-thiadiazoles, 1,2,3-thiadiazoles, 1,2,4-thiadiazoles, 1,2,4-triazoles, benzothiazoles, imidazoles, pyridines, pyrimidines, pyridazines, 1,2,4-triazolopyrimidines (e.g., [1,2,4]triazolo[1,5-a]pyrimidines & [1,2,4]triazolo[1,5-c]-pyrimidines), 1,2,4-triazolopyridazines, 1,2,4-triazolopyridines (e.g., [1,2,4] triazolo[1,5-a]pyridines), purines, pyrazolopyrimidines, oxazolylpyrazoles, 1,2,4-triazolo-1,2,4-triazoles, and the like.

The use of di(aromatic heterocyclyl) disulfide starting material compounds of Formula II wherein the two HET moieties are either the same or different is theoretically possible. Starting materials wherein the two HET moieties are different, however, are not readily obtainable, are not particularly stable, and would result in the co-preparation of two different chlorosulfonyl substituted aromatic heterocycle compounds of Formula I, which would have to be separated or used as a mixture. For these reasons, in the contemplated process of the invention, the two HET moieties of the compounds of Formula II are the same; that is, the contemplated starting material compounds of Formula II are symmetrical about the sulfur-sulfur bond.

The aromatic heterocyclic moieties HET are optionally substituted with a wide variety of typical substituents. Substituents that are tolerated include, for example, fluoro, chloro, bromo, iodo, lower alkyl (such as methyl, ethyl, pentyl, 1,1-dimethylethyl, and the like), halogenated lower alkyl (such as fluoromethyl, trifluoromethyl, dichloromethyl, 2,2,2-trifluoroethyl, 3-chloro-2,2-dimethylpropyl, and the like), lower alkoxy (such as methoxy, ethoxy, and 1-methylethoxy), halogenated lower alkoxy (such as 2-chloroethoxy, 1,1,2,2-tetrafluoroethoxy, dichloromethoxy, 2,2,2-trifluoroethoxy, and 1,1,2,3,3,3-hexafluoropropoxy), amino, (lower alkyl)-amino, di(lower alkyl)amino, (lower alkyl)sulfonyl, halogenated (lower alkyl)sulfonyl, carboxy, lower alkoxycarbonyl, aminocarbonyl, (lower alkyl)aminocarbonyl, di(lower alkyl) aminocarbonyl, cyano, nitro, optionally substituted phenyl, optionally substituted pyridinyl, optionally substituted phenoxy, optionally substituted pyridinyloxy, and the like.

The process is especially useful for the preparation of many optionally substituted chlorosulfonyltriazolopyrimidine compounds and the preparation of 2-chlorosulfonyl[1,2,4]triazolo[1,5-c]pyrimidine compounds from 2,2'-dithiobis([1,2,4]triazolo[1,5-c]-pyrimidine) compounds that are relatively insoluble in chlorinated hydrocarbon solvents and in aqueous hydro-chloric acid is a preferred application. The preparaton of optionally substituted 2-chlorosulfonyl-(5 or 8)-(methoxy or ethoxy)[1,2,4]triazolo[1,5-c]pyrimidine compounds, such as 2-chlorosulfonyl-8-fluoro-5-methoxy-[1,2,4]triazolo[1,5-c]pyrimidine, 2-chlorosulfonyl-5-ethoxy-7-fluoro[1,2,4]triazolo[1,5-c]pyrimidine, 2-chlorosulfonyl-5-ethoxy-7-methyl[1,2,4]triazolo[1,5-c]pyrimidine, and 2-chlorosulfonyl-5-methoxy-7-methyl-[1,2,4]triazolo[1,5-c]pyrimidine, is a more preferred application. The preparation of optionally substituted 2-chlorosulfonyl-(5 or 8)-methoxy[1,2,4]triazolo[1,5-c]-pyrimidine compounds, such as 2-chlorosulfonyl-8-fluoro-5-methoxy[1,2,4]triazolo[1,5-c]pyrimidine, is often of special interest.

The chlorosulfonyl substituted aromatic heterocycle compounds of Formula I produced by the process of the present invention are intermediates useful for the preparation of a variety of commercial and developmental pharmaceutical and agricultural products. They are typically condensed with aliphatic or aromatic amines to produce biologically active heterocyclic sulfonamide compounds.

The most distinctive feature of the process of the present invention is the presence of a phase transfer catalyst. Phase transfer catalysts have, surprisingly, been found to increase the rate of the chloroxidation reaction involved in the process and to improve the yield of the chlorosulfonyl substituted aromatic heterocycle compounds of Formula I produced. The increase in reaction rate that is observed allows the process to be carried out at a lower temperature and/or in a shorter period of time than previously known processes. Phase transfer catalysts of all types have been found to be useful in the process. Phase transfer catalysts that increase the solubility of chloride ion in the organic phase of the reaction medium are believed to be the most effective. Such phase transfer catalysts are sometimes referred to as chloride ion transfer agents. Suitable phase transfer catalysts include tetrahydrocarbylammonium salts, such as tetraethylammonium bromide, tetrapropylammonium chloride, tetrabutylammonium bisulfate, tetrahexylammonium chloride, phenyltrimethylammonium chloride, methyltripropylammonium bromide, benzyltriethylammonium chloride, tricaprylmethylammonium chloride, methyltrioctylammonium bromide, and the like. Many trihydrocarbylamine compounds behave in the same manner as tetrahydrocarbylammonium salts when they are in acidic media; that is, they are often effective phase transfer catalysts performing as chloride ion transfer agents. The medium of the process of the present invention may initially be acidic and, in any event, becomes strongly acidic as soon as the reaction proceeds. Trihydrocarbylamine compounds have been found to be effective phase transfer catalysts for the process. Tributylamine and trioctylamine, for example, are useful. Tetrahydrocarbylphosphonium salts, such as tetraphenylphosphonium chloride and tetrabutylphosphonium bromide, and crown ethers, such as dicyclohexano-18-crown-6, used with or without added inorganic salts, are also suitable phase transfer agents.

Tetrahydrocarbylammonium salts are typically preferred phase transfer catalysts and tetraalkylammonium salts (wherein benzyl is viewed as methyl substituted with phenyl and is an alkyl moiety) are generally more preferred because of their effectiveness, relatively low cost, and ease of removal from the reaction product. Tetraalkylammonium salt phase transfer catalysts having about 8 to about 34 total carbon atoms typically produce excellent results and those having about 10 to about 28 total carbon atoms are generally preferred. The anion of the tetrahydrocarbylammonium salt catalyst does not appear to be an important factor. The presence of large amounts of hydrochloric acid in the medium (formed during the reaction) results in chloride ion being the principal anion in the medium. Chloride, bromide, iodide, sulfate, bisulfate, nitrate, phosphate, and other common anions are suitable. Halide ions are generally preferred and chloride ion is typically more preferred. Tetrapropylammonium, tetrabutylammonium, tetrahexylammonium, tricaprylmethylammonium and methyltributylammonium halides are representative of the preferred catalysts. Under some circumstances, methyltributylammonium chloride is a specifically preferred catalyst.

An effective amount of the phase transfer catalyst is employed in the process. Amounts in the range of about 0.001 to about 0.2 moles of catalyst per mole of di(heterocyclyl) disulfide compound of Formula II are typical and it is often preferred to employ about 0.002 to about 0.05 moles. It is generally preferred from economic and waste control points of view to use as little catalyst as is necessary to achieve reasonably fast reaction rates and good yields.

Water-immiscible organic solvents that are unreactive under the reaction conditions of the process and in which the chlorosulfonyl substituted aromatic heterocycle compound of Formula I being produced is at least partially soluble are employed in the reaction medium. Chlorinated hydrocarbon solvents, such as dichloromethane, chloroform, tetrachloromethane, 1,2-dichloroethane, 1,1-dichloroethane, 1,1,1-trichloroethane, trichloroethylene, tetrachloroethylene, chlorobenzene, 1,2-dichlorobenzene, and the like, are usually preferred. Aliphatic chlorinated hydrocarbon solvents are typically more preferred. Dichloromethane is often the solvent of choice. It is usually advantageous to use a sufficient amount of the water-immiscible organic solvent to maintain the compound of Formula I being produced in solution at the conclusion of the reaction.

Water is a required element of the reaction medium. The water can be added totally or in part as a diluent in the di(heterocyclyl) disulfide of Formula II starting material or as aqueous hydrochloric acid. It is often advantageous to add some of the water in one or both of these ways. The chloroxidation reaction produces hydrogen chloride and, therefore, the aqueous phase of the medium is acidic immediately upon initiation of the chemical reaction. When the starting material of Formula II used possesses an acid sensitive substituent, such as a methoxy group, it is often deleterious to allow the concentration of hydrogen chloride in the aqueous phase of the medium to rise above about 12 molar. Better results are often obtained when the concentration of hydrogen chloride at the end of the reaction is in the 4 to 8 molar range. The amounts of water and hydrochloric acid employed in the medium of the process can easily be adjusted to arrive at a suitable final concentration of hydrochloric acid in the aqueous phase. The amount of water employed is usually about 0.1 to about 1 times the amount of water-immiscible organic solvent employed. It is generally preferred to use about 0.2 to about 0.5 times as much. Sufficient total reaction medium is used to create a fluid reaction mixture and to promote good mixing.

Chlorine is generally added to the reaction medium as a gas. It is typically added below the surface of the reaction medium and at as rapid a rate as possible while maintaining a relatively even distribution of the chlorine in the medium and maintaining the desired reaction temperature. The stoichiometry of the chloroxidation reaction requires five moles of chlorine per mole of di(heterocyclyl) disulfide of Formula II. At least about five moles are generally used. It is usually preferred to use a small excess of chlorine.

The reaction is carried out at a temperature at high enough that the chemical reaction of the process proceeds relatively rapidly and low enough that side reactions are minimized. Temperatures of about −20° C. to about 60° C. are suitable; temperatures of about −10° C. to about 30° are generally preferred. The reaction is exothermic and efficient cooling is generally required.

The reaction of the process takes place quickly and is generally complete within about 10 hours. The amount of time required is dependent on a variety of factors including the chemical and physical properties of the di(heterocyclyl) disulfide compound of Formula II, the temperature, the rate of chlorine addition, the organic solvent identity and amount, the amount of water, the catalyst identity and amount, the reactor geometry, and other factors known to those in the art. When the di(heterocyclyl) disulfide compound of Formula II being chloroxidized is quite insoluble in the medium, the reaction is essentially complete when the three-phase system (two liquid phases and a solid phase) becomes a two liquid phase system. It is generally preferred to carry out the reaction under conditions wherein the reaction takes place relatively rapidly and to recover the product chlorosulfonyl substituted aromatic heterocycle compound of Formula I from the reaction medium relatively rapidly in order to avoid product decompsition. Sodium or potassium bisulfite or sulfite is often added to the system immediately after the reaction is complete to destroy any unreacted chlorine present.

The chlorosulfonyl substituted heterocyle compounds of Formula I obtained as products in the process of the invention are generally recovered by first removing the aqueous phase of the reaction medium from the organic phase and retaining the organic phase. They can be used as a chemical intermediates in this form without further recovery or can be further recovered from the organic phase by conventional means. The compounds of Formula I prepared can be further recovered, for example, by removing the solvent and any other volatile components of the organic phase by evaporation or by distillation. They can be purified, if desired, by conventional means, such as by extraction with water or with organic solvents in which they are not appreciably soluble, by recrystallization from organic solvents, or by chromatography. Compounds of Formula I are generally obtained in about 85 to 96 percent of the theoretical yield in the process.

EXAMPLES

The following examples are presented to illustrate the process of the invention and should not be construed as limitations on the claims.

1. Preparation of 2-Chlorosulfonyl-8-fluoro-5-methoxy-[1,2,4]triazolo[1,5-c]pyrimidine A mixture of 29.9 g (grams) (75.1 mmol) (milli-mole) of 2,2'-dithiobis(8-fluoro-5-methoxy[1,2,4]triazolo[1,5-c] pyrimidine), 300 mL (milliliter) of dichloromethane, 100 mL of water, and 1.1 g (2.7 mmol, 3.6 mole percent) of tricaprylmethylammonium chloride (Aliquat* 336) was placed in a 1 liter reactor equipped with a thermometer, mechanical stirrer, dry-ice condenser, gas inlet tube, and cooling jacket connected to a bath. The mixture was cooled to −3° C. and then 29.4 g (415 mmol) of chlorine gas was added with stirring over a 2-hour period keeping the temperature at −3 to 5° C. The phases were then separated and the organic phase was analyzed by quantitative high pressure liquid chromatography and found to contain 137 mmol (91 percent of theory) of the title compound.

2. Preparation of 2-Chlorosulfonyl-7-fluoro-5-methoxy-[1,2,4]triazolo[1,5-c]pyrimidine A mixture of 5.0 g (13 mmol) of 2,2'-dithiobis-(7-fluoro-5-methoxy[1,2,4]triazolo[1,5-c]pyrimidine), 75 mL of dichloromethane, 25 mL of water, and 0.3 g (1.0 mmol) tetrabutylphosphonium chloride was cooled to 3° C. and 6.0 g (8.5 mmol) of chlorine gas was added with stirring and cooling. The mixture was allowed to react at 0 to 3° C. with stirring for 2 hours by which time the initial slurry had become clear leaving two liquid phases. The phases were separated and the organic phase was concentrated by evaporation under reduced pressure to obtain 7.5 g of the title compound in impure form as a white solid.
1 H NMR Spectrum (300 MHz) in CDCl$_3$: 6.96(s, 1 H), 5.29(s, 1 H), 4.40(s, 3 H).

3. Preparation of 2-Chlorosulfonyl-8-fluoro-5-methoxy-[1,2,4]triazolo[1,5-c]pyrimidine A mixture of 23.0 g (48 mmol) of 82.3 percent purity 2,2'-dithiobis(8-fluoro-5-methoxy[1,2,4]triazolo-[1,5-c] pyrimidine) containing 9 mmol of 8-fluoro-5-methoxy[1,2,4]triazolo[1,5-c]pyrimidine-2-thiol, 142 g of dichloromethane, 78.2 g of water, and 0.13 g (4 mmol) of 75 percent purity methyltributylammonium chloride was placed in a 250 mL flask equiped with a magnetic stirrer, a gas inlet with a polytetrafluoroethylene pipe extending below the surface of the liquid, a dry-ice cooled condenser, and a cooling jacket connected to a 21° C. recirculating bath. Chlorine gas (24.5 g, 370 mmol) was added over a 5-hour period with stirring and cooling at which time the solids present completely dissolved and the solution became greenish yellow. Ten grams (32 mmol) of 27 percent aqueous sodium bisulfite solution (10 g) were added and when the chlorine color disappeared, the phases were separated. The organic phase was concentrated by evaporation under reduced pressure ending at 55° C. under 40 millimeters Hg (5.3 kilopascals) pressure to obtain 28.3 g (94.4 percent of theory) of the title compound as a 92.5 percent purity white solid. The compound obtained was shown to be the same as that disclosed in U.S. Pat. No. 5,488,109.

A procedure very similar to that described above (using the same starting materials and catalyst), with the exception that the organic phase was analyzed by high pressure liquid chromatography to determine the yield instead of recovering the product, was carried out at a variety of temperatures. The results are given in the following table:

| Jacket Temperature*, ° C. | Catalyst Conc., Mole %# | Chlorine Addition Time, min | Reaction Time, min | Yield, Percent Theory |
|---|---|---|---|---|
| −1 | 1.6 | 207 | 272 | 92 |
| −1 | 0.8 | >227 | 480 | 88 |
| 6 | 1.6 | 214 | 278 | 91 |
| 6 | 0.8 | 212 | 315 | 90 |
| 6^ | 0.8 | 212 | 335 | 93 |
| 14 | 1.6 | 195 | 195 | 90 |
| 21^ | 0.8 | 297 | 297 | 94 | based on 2,2'-dithiobis(8-fluoro-5-methoxy[1,2,4]triazolo[1,5-c] pyrimidine)
*internal temperature about 2° C. higher
^1.35X scale of other experiments in table 4. Preparation of 2-Chlorosulfonyl-8-fluoro-5-methoxy-[1,2,4]triazolo[1,5-c]pyrimidine Using Phase Transfer Catalysts A mixture of 15 g (38 mmol) of 2,2'-dithiobis-(8-fluoro-5-methoxy[1,2,4]triazolo[1,5-c]pyrimidine), 150 mL of dichloromethane, 50 mL of water, and a phase transfer catalyst was placed in a 1 liter reactor equipped with a thermometer, mechanical stirrer, dry-ice condenser, gas inlet tube, and cooling jacket connected to a bath. The mixture was cooled to 3 to 5° C. and then 14.7 g (207 mmol) of chlorine gas was added with stirring over a 10 to 20-min period. Stirring was continued until the solids disappeared in some cases, for 7 hours in other cases, and in other cases, where the solids did not disappear, 6 or 8 hours. Any solids present were removed by filtration and the phases were separated and the organic phase was analyzed for the title compound by quantitative high pressure liquid chromatography. The results are given in the following table:

| CATALYST | #Mole Percent | Reaction Time, hr | Yield % |
|---|---|---|---|
| none | — | 6 | 16* |
| tetraethylammonium bromide | 20 | 7 | 91 |
| tetraethylammonium chloride | 5 | 6 | 67* |
| tetrapropylammonium bromide | 20 | 7 | 91 |
| tetrapropylammonium bromide | 5.4 | 7 | 94 |
| tetrabutylammonium bisulfate | 5 | 0.8 | 90 |
| tetrahexylammonium chloride | 5 | 0.7 | 95 |
| phenyltrimethylammonium chloride | 5.4 | 8 | 80* |
| tetraphenylphosphonium chloride | 5 | 2 | 97 |
| tetrabutylphosphonium chloride | 5 | 0.7 | 95 |
| 18-crown-6 ether with 1N sodium chloride | 5 | 6 | 40* |
| dicyclohexano-18-crown-6 ether | 5 | 3.4 | 96 |
| dicyclohexano-18-crown-6 ether with 1N sodium bromide | 5 | 3.2 | 96 |
| dicyclohexano-18-crown-6 ether with 1N sodium chloride | 5 | 2.8 | 96 |
| methyltributylammonium chloride^ | 0.4 | 7 | 83* |
| methyltributylammonium chloride^ | 0.7 | 5.0 | 90 |
| methyltributylammonium chloride^ | 1.6 | 4.6 | 91 |
| tri-(2-methylpropyl)amine with 1N hydrochloric acid | 32 | 4 | 98 |
| trioctylamine with 1N hydrochloric acid | 17 | 2 | 94 | based on 2,2'-dithiobis(8-fluoro-5-methoxy[1,2,4]triazolo[1,5-c]pyrimidine)
*incomplete
^similar, but not identical reaction conditions

What is claimed is:

1. A process for the preparation of a chlorosulfonyl substituted aromatic heterocycle compound of the formula:

HET-SO$_2$Cl wherein HET represents an optionally substituted 5- or 6-membered aromatic heterocyclic moiety which comprises contacting a di(aromatic heterocyclyl)-disulfide compound of Formula II:

HET-S—S-HET wherein HET is defined as hereinabove with chlorine in a medium comprising a water-immiscible organic solvent, water, and an effective amount of a phase transfer catalyst at a temperature of about −20° C. to about 60° C.

2. A process according the claim 1 wherein the phase transfer catalyst is a tetrahydrocarbylammonium salt, a tetrahydrocarbylphosphonium salt, or a crown ether.

3. A process according the claim 2 wherein the phase transfer catalyst is a tetraalkylammonium salt.

4. A process according to claim 3 wherein the tetraalkylammonium salt has a total number of carbon atoms between about 10 and about 28.

5. A process according to claim 4 wherein the tetraalkylammonium salt is a tetrapropylammonium, tetrabutylammonium, tetrapentylammonium, tetrahexylammonium, methyltripropylammonium, methyltributylammonium, or tricaprylmethylammonium halide.

6. A process according to claim 1 wherein about 0.002 to about 0.05 moles of catalyst per mole of di(aromatic heterocyclyl) disulfide compound is used.

7. A process according to claim 1 wherein the water-immiscible organic solvent is a chlorinated hydrocarbon solvent.

8. A process according to claim 7 wherein the chlorinated hydrocarbon solvent is dichloromethane.

9. A process according to claim 1 wherein the water contains hydrochloric acid initially.

10. A process according to claim 1 wherein the reaction is carried out at a temperature of about −10° C. to about 30° C.

11. A process according to claim 1 wherein the compound prepared is an optionally substituted chlorosulfonyltriazolopyrimidine compound.

12. A process according to claim 11 wherein the compound prepared is an optionally substituted 2-chlorosulfonyl [1,2,4]triazolo[1,5-c]pyrimidine compound.

13. A process according to claim 12 wherein the compound prepared is 2-chlorosulfonyl-8-fluoro-5-methoxy[1,2,4]triazolo[1,5-c]pyrimidine.

* * * * *